United States Patent
Hölscher et al.

(10) Patent No.: US 12,055,609 B2
(45) Date of Patent: Aug. 6, 2024

(54) METHOD AND CONTROL UNIT FOR COMPENSATION OF EDDY CURRENT INDUCED MAGNETIC FIELDS IN MAGNETIC RESONANCE IMAGING

(71) Applicant: Siemens Healthcare GmbH, Erlangen (DE)

(72) Inventors: Uvo Hölscher, Erlangen (DE); Michael Köhler, Nuremberg (DE); Daniel Niederlöhner, Erlangen (DE); Alto Stemmer, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 631 days.

(21) Appl. No.: 16/598,056

(22) Filed: Oct. 10, 2019

(65) Prior Publication Data

US 2020/0116807 A1    Apr. 16, 2020

(30) Foreign Application Priority Data

Oct. 16, 2018   (EP) .................... 18200639

(51) Int. Cl.
*G01R 33/385*   (2006.01)
*G01R 33/3875*  (2006.01)
(Continued)

(52) U.S. Cl.
CPC ....... *G01R 33/385* (2013.01); *G01R 33/3875* (2013.01); *G01R 33/446* (2013.01);
(Continued)

(58) Field of Classification Search
CPC .............. G01R 33/385; G01R 33/3875; G01R 33/446; G01R 33/56518; G01R 33/56; A61B 5/055
See application file for complete search history.

(56) References Cited

U.S. PATENT DOCUMENTS

| | | | |
|---|---|---|---|
| 4,647,858 A | 3/1987 | Bottomley | |
| 5,332,969 A * | 7/1994 | Tsuruno | G01R 33/3852 |
| | | | 324/309 |

(Continued)

FOREIGN PATENT DOCUMENTS

| | | | |
|---|---|---|---|
| DE | 102010035539 A1 | 3/2012 | |
| EP | 1004892 A1 * | 5/2000 | ....... G01R 33/56518 |

OTHER PUBLICATIONS

European Search Report for European Patent Application No. 18200639.5-1022 mailed Apr. 26, 2019.
(Continued)

*Primary Examiner* — Rishi R Patel
(74) *Attorney, Agent, or Firm* — Lempia Summerfield Katz LLC

(57) ABSTRACT

Eddy current induced magnetic fields (MF) are compensated in a magnetic resonance imaging system. An MR-sequence (M) includes a number of gradients. A dataset includes values of an amplitude and a time constant of eddy current fields of a number of gradients on at least one gradient axis. A number of points in time within the time period of the MR-sequence are defined. A number of constant currents are calculated for a number of coils of the magnetic resonance imaging system based on the dataset. The number of constant currents is designed to compensate at least at the one defined point in time (PT1, PT2). The calculated number of constant currents are applied on the related coils prior or during the application of the MR-sequence or a section of the MR-sequence.

17 Claims, 3 Drawing Sheets

(51) Int. Cl.
*G01R 33/44* (2006.01)
*G01R 33/56* (2006.01)
*G01R 33/565* (2006.01)
*A61B 5/055* (2006.01)

(52) U.S. Cl.
CPC ........ *G01R 33/56518* (2013.01); *A61B 5/055* (2013.01); *G01R 33/56* (2013.01)

(56) References Cited

U.S. PATENT DOCUMENTS

| | | | | |
|---|---|---|---|---|
| 5,770,943 | A * | 6/1998 | Zhou | G01R 33/56518 324/307 |
| 7,633,292 | B2 | 12/2009 | Gao | |
| 2004/0227513 | A1 | 11/2004 | Weissenberger | |
| 2010/0148774 | A1 | 6/2010 | Kamata | |
| 2012/0217966 | A1 | 8/2012 | Feiweier | |
| 2014/0112564 | A1 * | 4/2014 | Hsiao | G06T 11/60 382/131 |
| 2016/0091588 | A1 * | 3/2016 | Benner | A61B 5/055 324/309 |
| 2016/0274202 | A1 * | 9/2016 | Stemmer | G01R 33/56563 |
| 2017/0131372 | A1 | 5/2017 | Dewdney | |
| 2018/0011160 | A1 | 1/2018 | Greiser | |

OTHER PUBLICATIONS

Sengupta, Saikat, et al. "Software compensation of Eddy current fields in multislice high order dynamic shimming." Journal of Magnetic Resonance 210.2 (Jun. 2011): 218-227.

Bernstein, Matt A., Kevin F. King, and Xiaohong Joe Zhou. Handbook of MRI pulse sequences. Elsevier, 2004. pp. 316-331.

Elster Allen : "Active shimming" Questions and Answers in MRI, Sep. 26, 2018 (Sep. 26, 2018), XP093171063, pp. 1-3. Retrieved from the Internet: URL:https://web.archive.org/web/20180926202157/ https://mriquestions.com/active-shimming.html.

* cited by examiner

METHOD AND CONTROL UNIT FOR COMPENSATION OF EDDY CURRENT INDUCED MAGNETIC FIELDS IN MAGNETIC RESONANCE IMAGING

RELATED CASE

This application claims the benefit of EP 18200639.5, filed on Oct. 16, 2018, which is hereby incorporated by reference in its entirety.

FIELD

The present embodiments describe a method and a control unit for compensation of eddy current induced magnetic fields in a magnetic resonance imaging system, as well as a related magnetic resonance imaging system.

BACKGROUND

In the technical field of magnetic resonance imaging (MRI), there occurs the problem that magnetic fields generated by eddy currents can disturb the image quality of magnetic resonance (MR) measurements. Various methods address eddy currents as disclosed for instance in DE 102010035539 B4, U.S. Pat. No. 7,633,292 B2, and US 20180011160 A1.

Specifically, the formation of non-linear field disturbances generated by eddy currents, i.e. of "higher spatial orders", causes problems that cannot be easily compensated.

Eddy currents can be generated in MRI devices by temporal changes of magnetic fields, especially by the switching of gradient pulses. By temporally changing the magnetic field, each ramp of a gradient pulse can generate eddy currents in conductive structures located in an MRI scanner. These conductive structures can be any metal used in the MRI-device.

Eddy currents cause time-dependent magnetic fields, which in principle can have arbitrary geometries. After applying a ramp of a gradient pulse, which generates an eddy current, an exponential decay of the magnetic field generated thereby is often assumed for the sake of simplicity, following the equation:

$$B_{EC}(t) = G \cdot A \cdot e^{(-t/\tau)}. \quad (1)$$

wherein $B_{EC}(t)$ denotes the magnetic field generated by the eddy current, G denotes the change of the gradient amplitude during application of the ramp, A denotes a constant of proportionality, t the time and $\tau$ the time constant of the respective eddy current. For this equation, it is assumed that the time constant is long compared to the ramping time of the generating gradient, because then the amplitude of the eddy current at the end of the ramp is proportional to the gradient amplitude. In addition, the field errors generated by gradient pulses can have oscillatory components, but these are also superimposed on the exponential decay shown above. The oscillations may be e.g. caused by mechanical vibrations. However, they are neglected in the following considerations.

Since MR imaging strongly depends on well-controlled magnetic fields (i.e. the homogeneity of the B0 field and the linearity of the gradient field), any additional magnetic field is a problem for image quality. For example, they can result in image distortion, signal loss or insufficient fat saturation.

In the following, the problem is discussed with the example of fat saturation. Fat saturation is a well-known method in MR imaging to suppress the signals of fatty tissue in the human body. Many of the fat saturation methods are based on the principle of chemical shift. In this case, it is taken advantage of the fact that spins in fat molecules have a slightly different resonance frequency than spins in water molecules (i.e. the chemical shift). So it is possible to apply spectrally selective RF pulses (radiofrequency-pulses) that affect only the spins in fat molecules and not the spins in water molecules. A precondition for this method is that the basic homogeneity of the B0 magnetic field is significantly better than the resonance frequency difference (i.e. the chemical shift) between fat and water. At a basic magnetic field strength of 1.5 T, the frequency difference is about 210 Hz, so that it needs a B0 homogeneity significantly better than 210 Hz for an effective fat saturation. If this is not the case, e.g. due to inhomogeneities of the B0-field, there could be regions where water-spins have the resonance frequency fat would have without said inhomogeneities (B0 field is reduced in these regions). As a result, spectrally selective excitation can in total not only affect fat but also water. It is also possible that the spectral pulses could not affect either fat or water (for example, if the B0 field is increased in some regions due to inhomogeneities). Both cases are problematic for clinical imaging with fat saturation because the signal from water can disappear and the signal from fat can be maintained. Due to the spatial variation of the eddy currents, this situation usually occurs locally, for example at the edge of the field of view. Especially local incidents may possibly be misinterpreted as pathologies, since fat saturation basically works and only fails in some areas.

Depending on the geometry of the changing magnetic fields and the conductive structures, the eddy current fields can have different spatial distributions and thus cause different spatial orders of field disturbances. The emergence of spatial components that are neither constant nor linear as a function of location cause particular problems when looking for methods for their compensation.

Significant eddy currents are often generated by conductive structures in regions outside the volume which is enclosed by the gradient coil, i.e. outside of the examination volume. The magnetic fields generated by the gradient coil in these regions can be referred to as "stray fields" and are usually attempted to be minimized by designing the conducting elements in a special way. This approach provides a shielding of the gradient coil and is usually effective to reduce or minimize the occurrence of relevant eddy currents.

MR scanners also typically have the ability to dynamically compensate magnetic field distortions (e.g. normal field inhomogeneities induced by the patient or induced by eddy currents) that are a constant spatial function or linear as a function of a spatial coordinate (corresponding to zero or first spatial order). In principle, the system frequency and the gradients are influenced in order to compensate dynamic magnetic fields induced by eddy currents during an MR sequence. The biasing of the system frequency and the gradients must occur dynamically to compensate for the dynamics of the eddy currents.

Other types of solutions used so far are very specific to the particular application or for the particular MR sequence used for imaging. One example are EPI diffusion measurements (EPI: Echo Planar Imaging), where there are various compensation methods, since diffusion coding usually uses very strong gradient pulses, which can generate particularly strong eddy currents. In addition, EPI imaging is very susceptible to inhomogeneities in the B0 field, which can lead to ghosting or distortions of the reconstructed image. Known approaches relate to aspects of the measurement directly, e.g. use of bipolar diffusion gradients to achieve an extensive compensation of the resulting eddy currents by using a clever arrangement of the gradient ramps. Other approaches use registration of different images measured with different diffusion gradients to compensate for the different distortions due to different eddy currents.

A disadvantage of the state of the art is that many solutions for the compensation of eddy currents of higher spatial order are essentially very specific and can only be used in certain applications or with experimental hardware. A general compensation that is applicable with commonly available hardware and for various applications is not established up to this day. Especially, there is no general solution to the problems of spectral fat saturation caused by eddy currents that can be applied to various MR-sequences.

SUMMARY AND DESCRIPTION

MRI devices and methods are improved to facilitate a reduction and/or compensation of eddy current induced magnetic fields in a magnetic resonance imaging system.

Since a compensation in reality does typically not completely annihilate an effect (only in an ideal environment), "compensation" means to minimize or at least reduce the influence of eddy current induced magnetic fields on the measurements. Thus, the expression "reduction" also could be used.

This object is achieved by the method, a control unit, and a magnetic resonance imaging system (MRI-system) according to the claims.

The method according to one embodiment for compensation of eddy current induced magnetic fields in a magnetic resonance imaging system includes the following acts:
1) MR-Sequence An MR-sequence (magnetic resonance sequence) is provided. Such MR-sequence is well known and usually includes different parts like RF-pulses, readout windows and, especially, a number of gradients. Since the gradients generate eddy currents during their ramps, the MR sequence should include a number of gradients (or otherwise there may appear the case that there are no eddy currents that could be compensated).

A suitable MR-sequence should certainly show certain periods where there will appear eddy current induced field disturbances during application of this sequence. Furthermore, the MR-sequence should not be very sensitive to constant currents applied to (shim) coils.

For the embodiment it is very advantageous, if the point of time of all gradient ramps as well as the amplitudes of the respective gradients are well known. These information are used in the following calculations or process. As an alternative, information about average values and/or summaries of certain gradients could be used as well.
2) Dataset A dataset includes values to generate a number of constant currents designed to compensate magnetic fields induced by eddy currents of the gradients of the MR-sequence at least at one defined point in time on at least one gradient axis. These values could be values for the constant currents themselves. However, it is preferred that these values are values of the amplitude and the time constant of eddy current fields of a number of gradients on at least one gradient axis. For good results, the dataset should provide values for all gradients on all gradient axes. Since the amplitude of the eddy current induced field (that is generated by the gradient ramp) scales linearly with the amplitude of the gradient, the eddy current induced fields could be calculated for all gradients if the value for the amplitude of at least one gradient is well known. Thus, it is preferred that values to calculate an eddy current induced field for the amplitude of at least one gradient are provided by the dataset.

There are usually three gradient axes, referring to magnet coils for all three spatial dimensions. Since an MR-sequence may include as well gradients at the same time on different gradient axes as also gradients at different times, and since all these gradients may generate eddy currents, it is best to have information about the eddy currents generated by the gradients on all different axes.

Since the gradients of the actual MR sequence will cause eddy currents when applied, it is preferred that the datasets provide information about the amplitude and the time constant of eddy current fields of the gradients applied in the actual MR-sequence. However, to make a universal compensation possible, the dataset could alternatively or additionally provide information about the amplitude and the time constant of eddy current fields of a great number of gradients that could be applied in an arbitrary MR-sequence. By providing information about amplitudes and/or time constants of eddy current fields caused by many different gradients there is the special advantage that the amplitude and/or time constant of an eddy current field of an arbitrary gradient can be extrapolated from the known data. In a system where the amplitude of the eddy current induced field scales linearly with the amplitude of a gradient, there is only the need to know how to calculate the eddy current induced fields for a certain amplitude of a gradient, since with this knowledge the eddy current induced fields could be calculated for all other gradients.

It should be noted that the determination of an exact time constant is, although it is preferred, not necessary. As an alternative to the exact determination, the time constant could also be estimated or approximated. A typical value could be chosen, especially as long as the results for the current application exhibit only a mild dependency on the time constants for ranges of time constants expected for the current MR system, e.g. in the case the time constants of all eddy current fields usually are similar.

It is preferred that the dataset is determined with calibration measurements. These calibration measurements could be applied initially after manufacturing of a magnetic resonance imaging system, during the installation process of the scanner, at the beginning of a measurement or anytime (e.g. if internal or external preferences have been changed). The results of the calibration measurements are provided in form of said dataset. It is preferred that the calibration measurements are performed with an (arbitrary) Reference-MR-sequence that is typically different from an MR-sequence used for image acquisition.
3) Points in Time A number of points in time is defined within the period of the MR-sequence. These points of time are those, where the magnetic fields of the eddy currents should be optimally compensated. It is preferred to choose points of time where the respective MR-sequence is particularly sensitive to B0 field variations and hence to eddy current induced field perturbations.

The following calculations facilitate an optimization (minimization) of the field-distortion of the B0-field by eddy current induced magnetic fields in that they provide the required currents to be set for field compensation. It should be noted that, since the present embodiment is concentrating on defined points in time, there is no guaranty that during other points of time the field-distortion of the B0-field are optimized as well. It could also be worse or different for other points of time. However, if the defined points of time are chosen as preferred, the overall result will be optimized, since not every point of time of a measuring sequence is equally sensitive to field disturbances. For example, fat saturation pulses or the measurement of the k-space center are extreme sensitive to field disturbances.

4) Calculation of Constant Currents

A number of constant currents for a number of (correction) coils of the magnetic resonance imaging system are calculated. These coils generate magnetic fields which correspond to correction fields. The sum of the correction fields is designed to compensate magnetic fields induced by eddy currents of the gradients of the MR-sequence at least at one defined point in time.

Many MR systems have so-called shim coils to generate magnetic fields of higher spatial orders, e.g. second or third order. This is usually used to homogenize the static magnetic field against other field distortions than those generated by dynamically disturbing fields. These shim coils are preferred coils for applying said calculated currents. It is preferred that a number of constant currents for a number of shim coils of the magnetic resonance imaging system is calculated (that could then be referred to as "shim-currents"), wherein each constant current is applicable for one of these shim coils.

It should be noted that common MR scanners do not have the ability to drive the shim coils dynamically and sufficiently fast during an MR sequence to compensate for the dynamically generated field disturbances of higher spatial order. Thus, the present embodiment using constant currents is especially advantageous when using said shim coils.

5) Application of the Constant Currents

The calculated number of constant currents is applied on the related coils, preferably the shim coils. This application happens prior to or during the application of the MR-sequence or prior to or during a section of the MR-sequence, preferably directly before the beginning of the application of the MR-sequence (or a section) plus a predefined time ("stabilizing time") that is needed to render the additional constant field to be stable. It is preferred that the constant currents are applied prior the application of the MR-sequence or the respective section. This has the advantage that there is enough time to stabilize the fields induced by the constant currents. However in the case where at the beginning of the MR-sequence (or at another time) there is no need for a homogenized B0-field, the constant currents could preferably also be applied during the application of the MR-sequence or the respective section. This has the advantage that measuring time is not prolonged. The constant currents should at least be applied prior the point of time where a homogenized B0-field is needed.

It has to be noted that the constant current calculated in the preceding step is applied in addition to other (constant) currents that are applied due to other homogenization reasons (other than the compensation of the magnetic fields induced by eddy currents). Since the MR-sequence is typically the sequence applied for image recording, the method explained here is preferably part of the magnetic resonance imaging recording method, wherein the method according to the embodiment is performed prior to the actual data acquisition.

It is preferred to use a magnetic resonance imaging system that offers a higher order shim-functionality, i.e. shim coils able to compensate field inhomogeneities of higher spatial orders. Especially by using the shim coils, the eddy current induced magnetic field compensation described above could also be extended for higher spatial orders (depending on the efficiency of the shim system).

The compensation unit according to one embodiment is designed to perform the method and includes the following components:

A data interface for receiving data of an MR-sequence including a number of gradients. Surely it is not necessary that the MR-sequence itself is received, but at least data about the exact setup of the MR-sequence that should be applied, i.e. the times, shapes and amplitudes of gradients of the MR-sequence and especially also other signals of the MR-sequence.

A data interface for receiving and/or a memory for storing a dataset. This dataset includes values of the amplitude and the time constant of eddy current fields of a number of gradients on at least one gradient axis (if the constant currents are calculated from these values). Alternatively, the dataset includes values of a number of constant currents designed to compensate magnetic fields induced by eddy currents of the gradients of the MR-sequence at least at one defined point in time.

In case this dataset is provided by calibration measurements or by a data network, and does not have to be stored, there is no need for an (internal) memory. Otherwise, in the case all necessary data is stored in the (internal) memory, there is no need for an interface.

A data interface for receiving and/or a memory for storing a number of points in time within the MR-sequence. In case these points in time are provided externally, the data interface is used, and there is no need for an (internal) memory. In case all necessary points in time are stored in the (internal) memory, there is no need for an interface.

All data interfaces could be realized as one physical interface used to receive the necessary data. However, they could also be physically separated interfaces.

A processor unit designed to calculate a number of constant currents for a number of coils of the magnetic resonance imaging system. The number of constant currents is designed to compensate magnetic fields induced by eddy currents of the gradients of the MR-sequence at least at one defined point in time.

This processor unit is especially designed to calculate (a) amplitudes of magnetic fields induced by eddy currents of the gradients of the MR-sequence, based on the dataset, (b) a number of constant currents for a number of shim coils of the magnetic resonance imaging system, each constant current applicable for a shim-coil. The number of constant currents is designed to compensate the calculated amplitudes of magnetic fields induced by eddy currents of the gradients of the MR-sequence at least at one defined point in time.

A means for applying the calculated number of constant currents on the related (shim) coils prior or during the application of the MR-sequence.

A control unit according to one embodiment includes a compensation unit described above.

A magnetic resonance imaging system according to one embodiment includes a control unit described above. It is, therefore, designed to compensate eddy current induced magnetic fields according to the method described above.

The embodiments are based on the application of a constant magnetic field in addition to other homogenization fields. This special magnetic field is a constant magnetic field that shifts the fields in the MRI-system so that at special points of time the magnetic fields induced by eddy currents are compensated. Especially, according to some embodiments for a measuring sequence (i.e. the MR-sequence), special points of time (one single point or more) are defined and then a constant (shim-) condition is calculated that influences a measurement at these points of time in a positive manner. It is preferred that measurements at other sensitive points of time are not noticeably deteriorated. To achieve that, these other sensitive points of time are preferably further defined points of time, so that the compensating magnetic fields can also be calculated based on these additional points of time.

The units or modules of the control unit mentioned above can be completely or partially realized as software modules running on a processor of a control unit. A realization largely in the form of software modules can have the advantage that applications already installed on an existing system can be updated, with relatively little effort, to install and run these units of the present application. The object of the embodiments is also achieved by a computer program product with a computer program that is directly loadable into the memory of a control unit of an MRI-system, and which includes program units or instructions to perform the steps of the method when the program is executed by the control unit. In addition to the computer program, such a computer program product can also include further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts of the computer program product so that these can be read from and executed by a processor of a control unit. A processor can include one or more microprocessors or their equivalents.

Particularly advantageous embodiments and features are given by the dependent claims, as revealed in the following description. Features of different claim categories may be combined as appropriate to give further embodiments not described herein.

According to a preferred method, the dataset includes values of the amplitude and time constant of eddy current fields of a number of gradients on at least one gradient axis. The calculation of a number of constant currents is performed by the following acts:

Calculation of Magnetic Fields

In this act, amplitudes of magnetic fields induced by eddy currents of the gradients of the MR-sequence are calculated. This calculation is based on the dataset mentioned above, i.e. the values of the amplitude and the time constant of eddy current fields of a number of gradients.

After this calculation there will exist values for said magnetic fields over the relevant parts of the MR-sequence, preferably in form of a time dependent distribution. It is preferred that at least the amplitudes of magnetic fields induced by eddy currents of the gradients of the MR-sequence at the defined points of time are calculated, since these are the points of time where these fields should be compensated.

Calculation of Constant Currents

A number of constant currents for a number of (e.g. shim) coils of the magnetic resonance imaging system is calculated. Each constant current is preferably applicable for one of these coils. The sum of the magnetic compensation fields generated by the application of all the constant currents is designed to compensate the calculated amplitudes of magnetic fields induced by eddy currents of the gradients of the MR-sequence at least at one defined point in time.

A preferred method for calculation is described in the following:

Since the dataset includes values of the amplitude G and the time constant τ of eddy current fields of a number of gradients on at least one gradient axis, the magnetic field generated by the eddy current could be calculated by using equation (1) already mentioned above:

$$B_{EC}(t) = G \cdot A \cdot e^{(-t/\tau)}. \tag{1}$$

It should be noted that the constant of proportionality A does not need to be defined exactly. It could be set as A=1. In the later calculations, the value A is not relevant since during the calculation of the constant currents it will be cancelled in a mathematical fraction.

By using equation (1), a value for the magnetic field generated by the eddy currents during the calibration measurement (or the values from the dataset) $EC_{Calc}^{Cal}$ could be calculated as a sum over all relevant gradient ramps of the respective reference-MR-sequence, at least for the simple case that the calibration measurement is performed identical for all axes. However, the equation can also be used if the calibration measurement is not performed identically for all axes. As a simplification, it is assumed that the calibration measurement is performed by applying identical test gradient patterns on each gradient axis. Therefore, this calculation of $EC_{Calc}^{Cal}$ is valid for all three gradient axes (x, y, z). Alternatively, it is also possible to apply different test gradient patterns on different gradient axes, which leads to an axis-specific value of $EC_{Calc}^{Cal}$. The term "test gradient" refers to those gradient pulses of the calibration measurement for which the generated eddy current induced fields are measured. MR sequences for this approach are available in the prior art and are known to those skilled in the art.

By using equation (16) and the actual MR-sequence, a value of the magnetic field generated by the eddy currents during the sequence $EC_{Calc}^{Seq}(\text{Axis})$ could be calculated as a sum over all relevant gradient-ramps of this MR-sequence on one axis. For each ramp, equation (1) is used. It should be noted that above value $EC_{Calc}^{Cal}$ gives a common value of all gradient axes (for the calibration), wherein the value $EC_{Calc}^{Seq}(\text{Axis})$ generally provides an individual value for each axis (for the MR-sequence), as in a general case MR sequences used for imaging apply different gradient pulses on different axes. This is due to the preferred approach that the calibration sequence applies the same pattern of relevant gradients on all spatial axes.

As a further embodiment, value $EC_{Measured}^{Cal}(\text{Axis, Order})$ is given to depend on the Axis as well as on the spatial order. It should be noted that the value A from equation (1) is included in this value $EC_{Measured}^{Cal}(\text{Axis, Order})$. Thus, value A is part of the determination of the magnetic field without the need to know A directly. The eddy current induced fields measured with a calibration sequence can be decomposed into different spatial base functions (i.e. different spatial orders). Preferably, at least some of the chosen base functions correspond to the spatial distributions of the magnetic fields generated by the individual shim coils. Then, the result of the calibration sequence measurement $EC_{Measured}^{Cal}(\text{Axis,Order})$ reflects the results where the relevant (test-) gradients are applied on individual axes and the measured fields are decomposed into well-suited spatial base functions.

Now, the eddy current induced field of the actual MR-sequence decomposed into spatial base functions or spatial orders, $EC_{Real}^{Seq}(\text{Order})$, can be calculated by the following equation:

$$EC_{Real}^{Seq}(\text{Order}) = \sum_{X,Y,Z} \frac{EC_{Measurement}^{Cal}(\text{Axis, Order}) \cdot EC_{Calc}^{Seq}(\text{Axis})}{EC_{Calc}^{Cal}}, \tag{2}$$

wherein the sum is performed over all three gradient axes X, Y and Z.

After that, the current is calculated for every shim coil compensating the field of a certain spatial order. Since every shim coil produces a well-defined field for a given current, this step is well known to the skilled person.

The calculated shim currents are applied in addition to shim currents used for compensating other effects. They are applied during the whole MR-sequence or at least during a predefined section of the MR-sequence.

By applying the current, the shim coils compensate the eddy current induced inhomogeneities of the B0-field at least during predefined points of time (that could repeat during the MR-sequence).

A complete calculation of the eddy current induced fields is preferably performed for every gradient axis, since a change in current on one gradient axis could theoretically produce an arbitrary field distribution on one of the other axes. Often gradient pulses applied on the x-axis produce very strong eddy current induced fields that mainly vary along the x-axis, but they may create eddy current fields which vary along the y-axis ("cross terms") or other spatial orders.

A development in spatial orders (or base functions) has two advantages for the calculation: On the one hand, the problem is rendered mathematically easier and on the other hand the solution is rendered such that it is easy to calculate which current is needed in the shim coils for compensation, since the shim coils often generate fields in the shape of base functions.

According to a preferred method, the dataset includes values of a number of spatial orders of an amplitude of eddy current fields of a number of spatial separated gradients on at least two gradient axes.

It should be noted that a gradient on one gradient axis could in principle generate eddy current induced fields in arbitrary spatial orders, so that e.g. a gradient on the x-axis could generate eddy current induced fields in the y-direction. However, each gradient generates the fields independently from the other gradients (potentially with individual time constants for each spatial component). Thus, the eddy current induced fields on the axes are sums of the contributions of the gradients applied on the axes.

It is preferred that amplitudes of magnetic fields induced by eddy currents of the gradients of the MR-sequence are calculated based on the spatial orders of an amplitude of eddy current fields, in particular concerning spatially separated gradients on gradient axes.

It is also preferred that constant currents for a number of shim coils are calculated based on the spatial orders of an amplitude of eddy current fields, in particular concerning spatially separated gradients on gradient axes. After the calculation, the calculated constant currents should be applied to the shim coils. Each current compensating a spatial order should be applied to the shim coil designed to compensate the respective spatial order.

According to a preferred method, a point of time is selected from the group includes: the point of time of a fat saturation pulse, the point of time of a water saturation or excitation pulse and the point of time of a k-space center of the given MR sequence. Depending on the goal of the measurement, it is preferred that more than one point of time is defined in the MR-sequence.

In a preferred method, the calculation of the amplitudes of magnetic fields induced by eddy currents of the gradients of the MR-sequence includes the actual parametrization of the measurement protocol, preferably the number of slices and/ or the thickness of the slices and/or the orientation of the slices and/or the field of view and/or the resolution.

According to a preferred method, the calculation of a number of constant currents for a number of coils is designed to compensate magnetic fields at different points in time. An average value for each constant current is chosen concerning the compensation at every chosen point in time.

According to a preferred method, two or more points in time are chosen and the constant currents for a number of coils are calculated such that for one point in time not the best compensation is chosen, but in total the best compensation for all points in time.

Preferably, the quality of measurements is calculated for each point in time in dependence of the degree of compensation at this point in time and after that the compensation is designed such that average or weighted average constant currents are applied so that the amelioration for measurements for each point in time meet at an average value. Thus, the calculation seeks for a weighting between the improvement for the measurements at one point in time and a worsening for the measurements at the other point(s) in time. The weighting will be performed by using an optimizing criterion, e.g. quality of fat saturation, quality of the images.

According to a preferred method, after the application of the calculated number of constant currents on the related coils, there is included a predefined stabilizing time until the MR-sequence is applied. This is advantageous to stabilize the fields of the coils.

According to a preferred method, in the case the MR-sequence includes two or more sections, preferably having different gradient patterns and/or different points of time. Different sections include different gradients, Points in time are chosen in different sections. The calculation and application of a number of constant currents is done separately for respective gradients and points in time of different sections of the MR-sequence. The same is advantageous, in the case where different points in time are chosen in different sections of an MR-sequence, e.g. fat saturation in one section and k-space-center in another section. In the case there is a dead time between two sections, this dead time could advantageously be used as stabilizing time for the application of the constant currents.

Since the MR-sequence and the relevant dataset are already known, the method according to one embodiment is performed on different sections of the MR-sequence. Especially when in a section the eddy currents at sensible points in time are similar, but different in different sections. The sections should be much longer than the response time of the constant currents applied to the coils so that the currents really could be estimated to be constant during a section and not be pseudo-constant.

This preferred method is especially advantageous in the case the gradient activity during a MR-sequence changes in well-defined sections and these sections are considerably longer than the switching times and/or saturation times of the coils (e.g. the shim-coils). An example is a EPI diffusion measurement, wherein the diffusion gradients are applied with different amplitudes during different sections of the MR-sequence (e.g. to measure different b-values) or wherein the diffusion gradients are applied in different manner on the gradient axes (e.g. to measure different diffusion directions).

For every section, a set of constant currents is preferably calculated and applied at the different sections, preferably together with the application of certain stabilizing times as described above.

According to a preferred method, the method is repeated for two or more similar MR-sequences or similar sections of an MR-sequence. Information of the calculated currents for the individual MR-sequences or sections are stored, and the stored values are applied without again calculating the currents in the case the respective MR-sequence or section is applied again.

According to a preferred method, between two different MR-sequences or sections of an MR-sequence at the time of changing a constant current for the coils, a pause or dummy measurement is applied (pulses and gradients are applied but no data is taken) or changing the acquisition of lesser important parts of the image dataset are performed, e.g. measurements of lesser importance are performed (e.g. measurements of the edge of k-space).

BRIEF DESCRIPTION OF THE DRAWINGS

Other objects and features of the present embodiments will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION OF THE PREFERRED EMBODIMENTS

Figure 1:
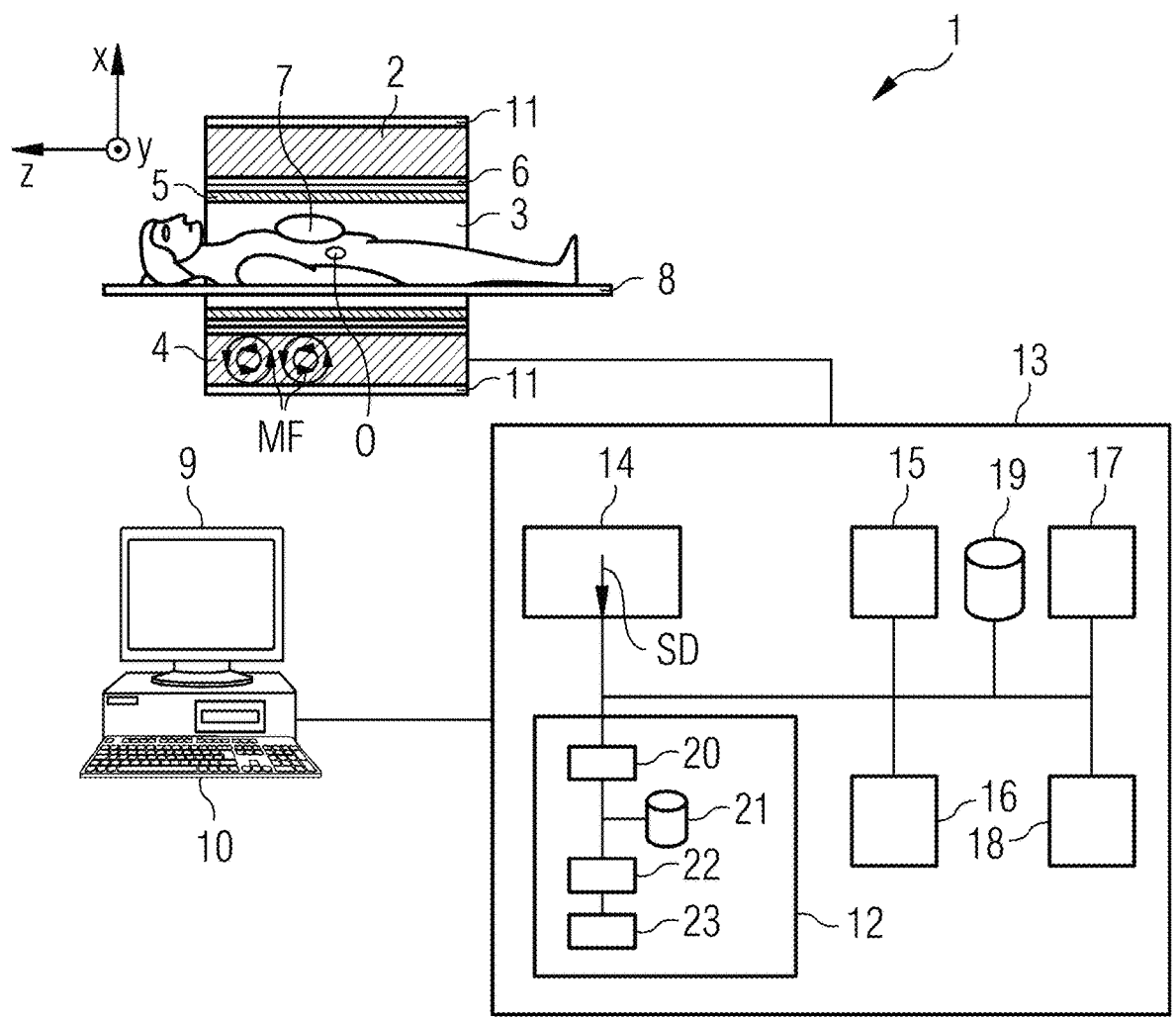
FIG. 1 shows a simplified MRI system according to an embodiment.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8, in whose body the actual examination object O is located.

The magnetic resonance scanner 2 is typically equipped with a basic field magnet system or B0 coil 4, a gradient system or gradient coils 6 as well as an RF transmission antenna system or whole body coil 5 and an RF reception antenna system or local coils 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another. In addition, the magnetic resonance scanner 2 includes shim coils 11, which may be formed in a conventional manner.

In the body of the basic field magnet system 4, there are shown magnetic fields MF that are induced by eddy currents from applied gradients.

The MRI system 1 shown here is a whole-body system with a patient tunnel into which a patient can be completely introduced. However, in principle, embodiments can also be other MRI systems, for example with a laterally open, C-shaped housing, as well as in smaller magnetic resonance scanners in which only one body part can be positioned.

Furthermore, the MRI system 1 has a central control device or controller 13 that is used to control the MRI system 1. This central control device 13 includes a sequence control unit or controller 14 for measurement sequence control. With this sequence control unit 14, the series of radio-frequency pulses (RF pulses) and gradient pulses can be controlled depending on a selected MR-sequence M (see FIG. 2) or, respectively, a series of multiple MR-sequences M to acquire magnetic resonance images within a measurement session. For example, such a series of MR-sequences M can be predetermined within a measurement or control protocol. Different control protocols for different measurements or measurement sessions are typically stored in a memory 19 and can be selected by an operator (and possibly modified as necessary) and then be used to implement the measurement.

To output the individual RF pulses of an MR-sequence M, the central control device 13 has a radio-frequency transmission device or transmitter 15 that generates and amplifies the RF pulses and feeds them into the RF transmission antenna system 5 via a suitable interface (not shown in detail). To control the gradient coils of the gradient system 6, the control device 13 has a gradient system interface 16. With this gradient system interface 16, for example, the shim coils 11 could also be driven, since the gradient coils are used to set the DC offset currents to shim the B0 field (i.e. to compensate the linear component of the field distortions). The sequence control unit 14 communicates in a suitable manner (for example via emission of sequence control data SD) with the radio-frequency transmission device 15 and the gradient system interface 16 to emit the MR-sequences M.

Moreover, the control device 13 has a radio-frequency reception device or receiver 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the MR-sequences M.

A reconstruction unit or processor 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit or display 9, and measurements can be planned and started by the input unit (possibly in combination with the display unit 9), and in particular suitable control protocols can be selected (and possibly modified) with suitable series of MR-sequences M as explained above.

The control unit 13 includes a compensation unit or processor 12 designed to perform the method. This compensation unit 12 includes the following components.

A data interface 20. This data interface is in this example designed to receive an MR-sequence M as well as a number of points in time PT1, PT2 within the MR-sequence M. For example, a user can choose an MR-sequence M by using the terminal 10 and manually include points in time PT1, PT2 (see FIG. 2) in the chosen MR-sequence M. However, a user could also enter the data for the following examination and the system automatically chooses an appropriate MR-sequence M stored in the memory 19 together with predefined points in time PT1, PT2.

A memory 21, where a dataset D is stored and includes values of the amplitude and the time constant of eddy current E1, E2, E3 fields of a number of gradients G on at least one gradient axis. In this memory 21, predefined points in time PT1, PT2 could also be stored.

Figure 4:
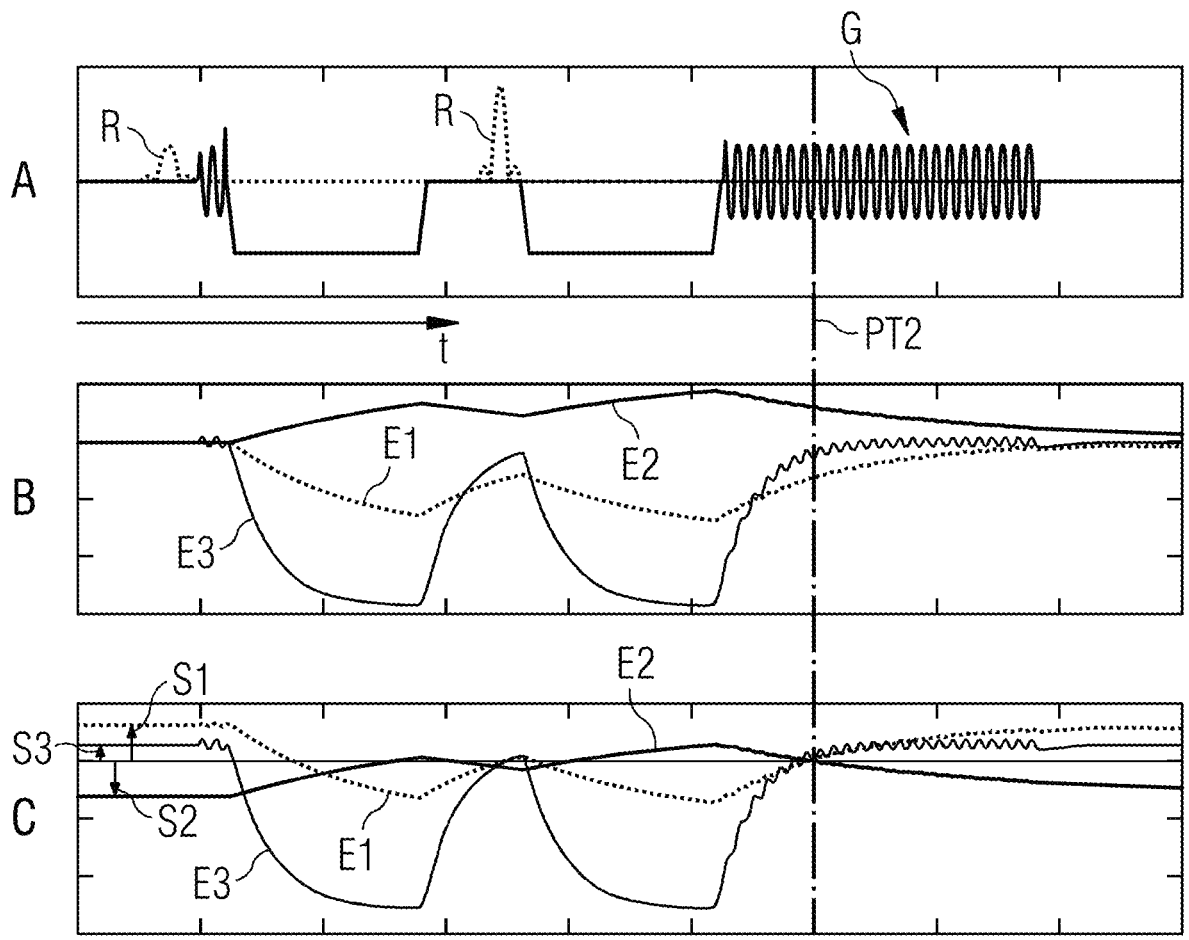
FIG. 4 illustrates the aim of one embodiment.
Figure 5:
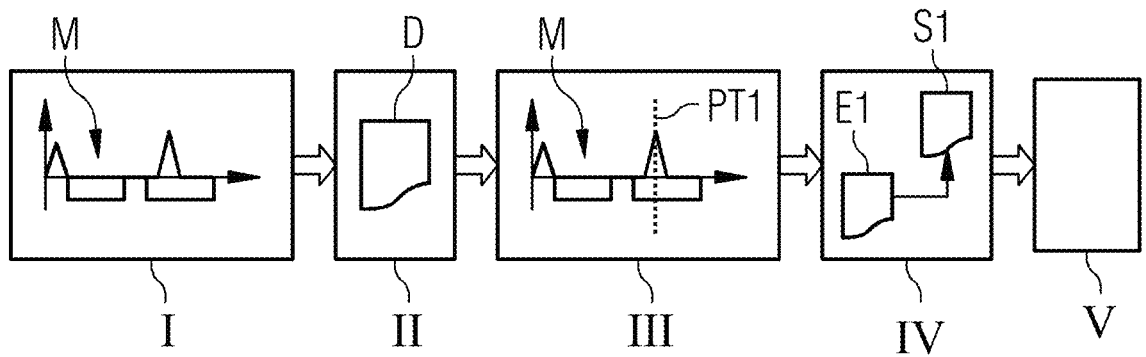
FIG. 5 shows a block diagram of the process flow of a preferred method according to one embodiment.

A processor unit or processor 22 designed to calculate a number of constant currents S1, S2, S3 (see FIG. 4) for a number of coils 11 of the magnetic resonance imaging system 1 based on the dataset D (see FIG. 5). The number of constant currents S1, S2, S3 is designed to compensate magnetic fields MF induced by eddy currents E1, E2, E3 of the gradients G of the MR-sequence M at least at one defined point in time PT1, PT2.

Means 23 for applying the calculated number of constant currents S1, S2, S3 on the related coils 11 prior or during the application of the MR-sequence M. The means 23 may be an interface, such as the gradient coil interface 16, a current source, a transmitter, or other current generating device or circuit.

The MRI system 1 according to one embodiment, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
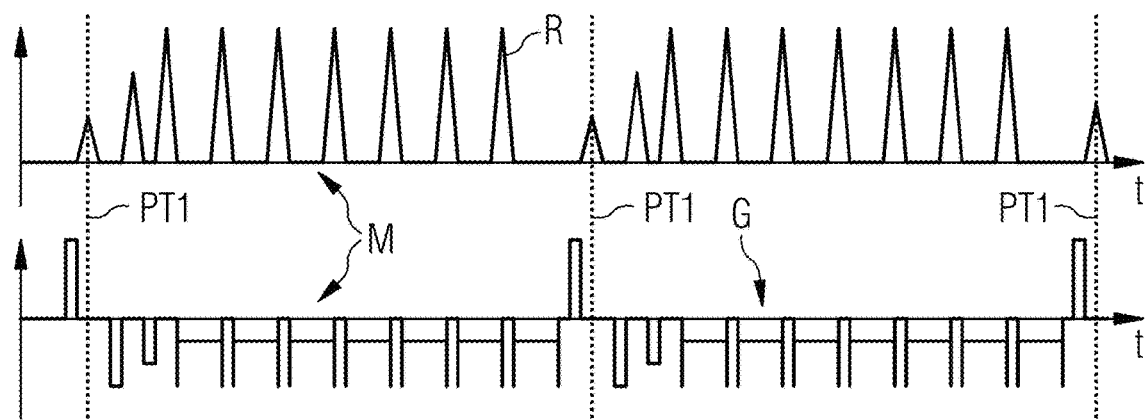
FIG. 2 shows an exemplary MR-sequence.

FIG. 2 shows a part of a TSE sequence (TSE: Turbo Spin Echo) with spectral fat saturation as an exemplary MR-sequence M. The time-axis t runs from left to the right. In the upper diagram, the RF-Pulses R are shown, in the lower diagram, gradients G are shown in the direction of the readout (here e.g. the x-axis). The other two gradient axes are not shown. In this figure, a point of time PT1 is chosen in the center of fat saturation. At this point of time PT1, compensation of eddy-current induced magnetic fields MF is advantageous, since spectral fat saturation is sensitive on fluctuations in the B0 magnetic field.

Figure 3:
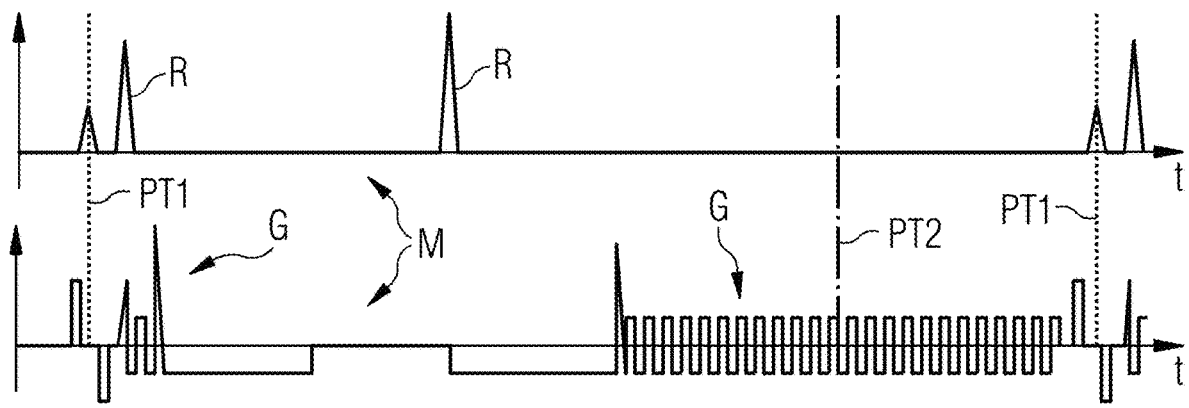
FIG. 3 shows another exemplary MR-sequence.

FIG. 3 shows a part of an EPI diffusion-sequence (EPI: Echo Planar Imaging) with spectral fat saturation as another exemplary MR-sequence M. In the upper diagram, the RF-Pulses R are shown, in the lower diagram, gradients G are shown in the direction of measurement (here e.g. the x-axis). The other two gradient axes are not shown. In this figure, two different points of time PT1, PT2 are chosen, first the center of fat saturation and second the center of the EPI measuring gradients. At these points of time PT1, PT2, compensation of eddy-current induced magnetic fields MF is advantageous. Especially the compensation in the k space center is advantageous to prevent spatial distortions.

It should be noted that typically a series of preparation scans are applied before the actual measurement. The RF- and gradient pulses are applied, however, no data is recorded or the recorded data is not used for reconstruction (i.e. the data is maybe used for calibration). As a result, the eddy current induced magnetic fields MF are already in steady state during the relevant points of time PT1, PT2. These preparation scans are not necessarily part of the MR-sequence M. In fact, the preparation scans could be used for calibration, however, the constant currents are not necessarily applied before the preparation scans.

FIG. 4 illustrates the aim of one embodiment. In this figure, three diagrams are shown, wherein the first diagram A shows an exemplary MR-sequence M that is a diffusion sequence that is similar to the MR-sequence M shown in FIG. 3. As single point in time PT2 the k-space center is chosen (dash-dotted line). It should be noted that this point in time is not positioned right in the center of the echo train since there are asymmetries due to partial fourier. The RF-Pulses R are shown dashed, one gradient axis G (read gradient) is shown solid.

The second diagram B shows calculated eddy currents E1, E2, E3 for three spatial orders (i.e., corresponding to different spatial base functions). It can be seen that the three spatially different eddy currents have different amplitudes, signs and time constants. In the chosen point of time PT1, all of these eddy currents E1, E2, E3 are different from zero and hence contribute to B0 inhomogeneities.

The third diagram C shows a superposition of the eddy currents and the static compensation. Constant currents S1, S2, S3 have been calculated for the shim coils 11 (see e.g. FIG. 1). These constant currents generate constant compensation fields which can be represented in the figure as offsets (arrows) to the eddy currents E1, E2, E3 in all three spatial orders. It can be seen that with this compensation in the chosen point of time PT1, there is not distortion any more.

FIG. 5 shows a block diagram of the process flow of a preferred method for compensation of eddy current E1, E2, E3 induced magnetic fields MF in a magnetic resonance imaging system 1.

In act I, an MR-sequence M is provided. The MR-sequence includes a number of gradients G. Concerning the MRI system shown in FIG. 1, this MR-sequence M could be provided by the terminal 10 or the memory 19 of the control unit 13.

In act II, a dataset D is provided. The dataset D includes values of the amplitude and the time constant of eddy current E1, E2, E3 fields of a number of gradients G on at least one gradient axis.

In act III, a number of points in time PT1, PT2 are defined within the time period of the MR-sequence M. FIGS. 2, 3 and 4 show exemplary points in time PT1, PT2.

In act IV, a number of constant currents S1, S2, S3 is calculated. This is done here with two steps.

First, amplitudes of magnetic fields MF induced by eddy currents M1, M2, M3 of the gradients of the MR-sequence M are calculated, based on the dataset D.

Second, a number of constant currents S1, S2, S3 for a number of coils 11 of the magnetic resonance imaging system 1 are calculated. Each constant current S1, S2, S3 is applicable for one of these coils 11. The number of constant currents S1, S2, S3 is designed to compensate the calculated amplitudes of magnetic fields MF induced by eddy currents E1, E2, E3 of the gradients G of the MR-sequence M at least at one defined point in time PT1, e.g. as shown in FIG. 4.

In act V, the calculated number of constant currents S1, S2, S3 is applied on the related coils 11 prior or during the application of the MR-sequence M.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method for compensation of eddy current induced magnetic fields in a magnetic resonance imaging system, the method comprising:
providing an MR-sequence comprising gradients, the gradients varying over time,
providing a dataset comprising values to generate constant currents designed to compensate magnetic fields induced by eddy currents of the gradients of the MR-sequence with a constant offset of the eddy currents,
defining at least one point in time within a time period of the MR-sequence on at least one gradient axis,
calculating the constant currents for coils of the magnetic resonance imaging system based on the dataset, wherein the constant currents are constant over the time during which the gradients vary and are designed to compensate magnetic fields induced by eddy currents of the gradients of the MR-sequence at the at least one defined point in time,
applying the calculated constant currents on the coils prior or during the application of the MR-sequence or a section of the MR-sequence.

2. The method according to claim 1, wherein the dataset comprises values of amplitudes of the magnetic fields induced by the eddy currents of the gradients on at least one gradient axis, wherein the calculation of the constant currents comprises:
calculating amplitudes of the magnetic fields induced by the eddy currents of the gradients of the MR-sequence, based on the dataset, and
calculating the constant currents for the coils of the magnetic resonance imaging system.

3. The method according to claim 2 wherein the dataset comprises a time constant, and wherein calculating the constant currents comprises calculating each constant current applicable for one of the coils, wherein the constant currents are designed to compensate the calculated amplitudes of the magnetic fields induced by the eddy currents of the gradients of the MR-sequence at the at least one defined point in time.

4. The method according to claim 1, wherein the dataset comprises values of spatial orders of amplitudes of the magnetic fields induced by the eddy currents of a number of spatially separated gradients on at least two gradient axes.

5. The method according to claim 4 wherein the amplitudes of the magnetic fields induced by the eddy currents are calculated, based on the spatial orders of the amplitude of the magnetic fields induced by the eddy currents for spatial separated gradients on gradient axes, wherein the coils comprise shim coils, and wherein the constant currents for a number of the shim coils are calculated based on the spatial orders of the amplitude of the magnetic fields induced by the eddy currents, for the spatial separated gradients on gradient axes, and wherein the calculated constant currents are applied to the shim coils designed to compensate the respective spatial order.

6. The method according to claim 1, wherein one of the at least one point in time is selected from the group comprising the point in time of a fat saturation pulse, the point in time of a water saturation or excitation pulse and the point in time of a k-space center.

7. The method according to claim 2, wherein the calculation of the amplitudes of the magnetic fields induced by eddy currents comprises actual parametrization of a measurement protocol for a number of slices, a thickness of the slices, an orientation of the slices, the field of view, and/or the resolution.

8. The method according to claim 1, wherein the at least one point in time comprises multiple points in time, wherein the calculation of the constant currents for the coils is designed to compensate the magnetic fields induced by the eddy currents at different ones of the multiple points in time, wherein an average value for each constant current is chosen concerning the compensation at every chosen of the multiple points in time.

9. The method according to claim 8, wherein two or more of the multiple points in time are chosen and the constant currents for the coils are calculated such that for one point of the two or more of the multiple points in time not a best compensation is chosen, but in total a best compensation for all the two or more of the multiple points in time.

10. The method according to claim 9, wherein a quality of measurements is calculated for each point of the multiple points in time in dependence of a degree of compensation at this point of the multiple points in time and after that the compensation is designed such that an average or weighted average of the constant currents is applied so that the quality of measurements for each of the multiple points point in time meets at the average value for each constant current.

11. The method according to claim 1, wherein after the application of the calculated constant currents on the coils, there is included a predefined stabilizing time until the MR-sequence is applied.

12. The method according to claim 1, wherein the at least one point in time comprises multiple points in time, wherein the MR-sequence comprises two or more sections, wherein different sections comprise different gradients and wherein different ones of the multiple points in time are chosen in different sections, and wherein the calculation and application of the constant currents is done separately for respective gradients and the points in time of different sections of the MR-sequence.

13. The method according to claim 1, wherein the method is repeated for two or more MR-sequences or sections of an MR-sequence, wherein values of the calculated constant currents for the two or more MR-sequences or sections are stored and the stored values are applied without again calculating the constant currents in the case the respective MR-sequence or section is applied again.

14. The method according to claim 13, wherein between two different ones of the MR-sequences or sections of the MR-sequence, a pause or dummy measurements is applied:
at a time of changing the constant current for the coils, and/or
at a time of changing an acquisition of lesser important parts of the dataset are performed.

15. A control system comprising a compensation processor, the control system comprising
a data interface for receiving an MR-sequence comprising gradients,
a data interface for receiving and/or a memory for storing a dataset comprising values of an amplitude and a time constant of eddy current fields of the gradients on at least one gradient axis, or comprising values of constant currents configured to compensate magnetic fields induced by the eddy currents of the gradients of the MR-sequence at least at one defined point in time, a processor configured to calculate the constant currents for coils of a magnetic resonance imaging system based on the dataset, wherein the constant currents are configured to be constant over time during which the gradients vary and compensate the magnetic fields induced by the eddy currents of the gradients of the MR-sequence at least at the one defined point in time, a gradient system interface for applying the calculated constant currents on the coils prior or during the application of the MR-sequence or a section of the MR-sequence.

16. The control system of claim 15, further comprising:
a magnetic resonance imaging system comprising the coils.

17. A non-transitory computer-readable medium on which is stored program instructions that can be read and executed by a computer, the instructions comprising:

providing an MR-sequence comprising gradients, providing a dataset comprising values to generate constant currents designed to compensate magnetic fields induced by eddy currents of the gradients of the MR-sequence, the constant currents being offsets constant over variation of the eddy currents, defining at least one point in time within a time period of the MR-sequence on at least one gradient axis, calculating the constant currents for coils of the magnetic resonance imaging system based on the dataset, wherein the constant currents are designed to compensate the magnetic fields induced by the eddy currents of the gradients of the MR-sequence at the at least one defined point in time, and applying the calculated constant currents on the coils prior or during the application of the MR-sequence or a section of the MR-sequence.

* * * * *